United States Patent [19]

Yamauchi et al.

[11] 4,188,117
[45] Feb. 12, 1980

[54] METHOD AND APPARATUS FOR DETECTING LEAKS IN HOLLOW FIBER MEMBRANE MODULES

[75] Inventors: Kazuhisa Yamauchi, Kyoto; Taku Tanaka; Syuji Kawai, both of Kurashiki, all of Japan

[73] Assignee: Kuraray Co., Ltd., Kurashiki, Japan

[21] Appl. No.: 900,582

[22] Filed: Apr. 27, 1978

[30] Foreign Application Priority Data

Apr. 28, 1977 [JP] Japan .................................. 52-50416

[51] Int. Cl.$^2$ ........................................... G01N 21/16
[52] U.S. Cl. ..................................... 356/237; 356/129
[58] Field of Search ............... 73/49, 3; 356/128, 129, 356/240, 362, 237

[56] References Cited

U.S. PATENT DOCUMENTS

| | | | |
|---|---|---|---|
| 2,362,235 | 11/1944 | Barnes | 356/129 |
| 2,968,209 | 1/1961 | Avlin | 356/129 |
| 3,468,610 | 9/1969 | Muffoletto | 356/129 |
| 3,736,790 | 6/1973 | Pontello | 356/237 |

*Primary Examiner*—John K. Corbin
*Assistant Examiner*—R. A. Rosenberger
*Attorney, Agent, or Firm*—Barry Kramer

[57] ABSTRACT

Leaks from a hollow fiber membrane module comprising a housing having one or more hollow fiber bundles positioned therein with at least one end of each bundle being sealed by a cementing layer includes the step of applying a pressurized gas to the external surfaces of the hollow fibers. The gas which is used must have a refractive index different from the refractive index of the ambient atmosphere. The atmospheric volume adjacent the sealed end of the module is optically monitored for refraction patterns caused by gas leaking through the sealed end into the volume. The optical system includes a light source and components for directing light from the source along an optical path including the monitored volume. Light which is passed through the monitored volume is directed to an optical display where the refraction patterns of the leaking gas will be visible. The method and apparatus permit leaks to be located without the use of liquids.

8 Claims, 14 Drawing Figures

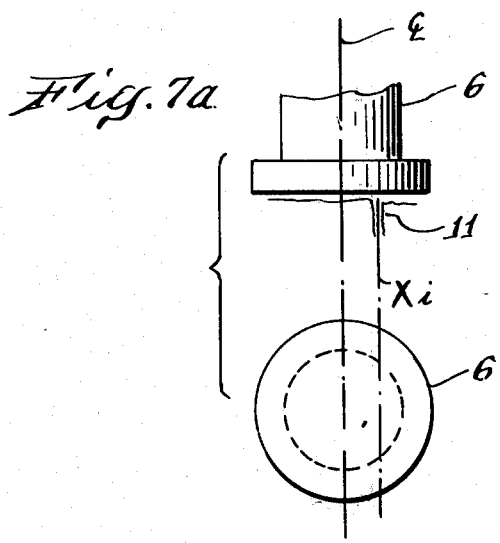
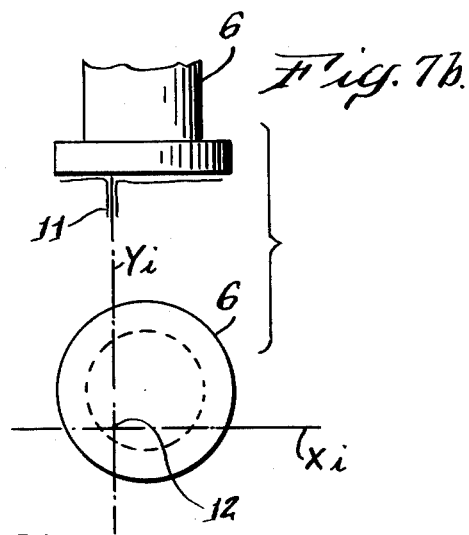
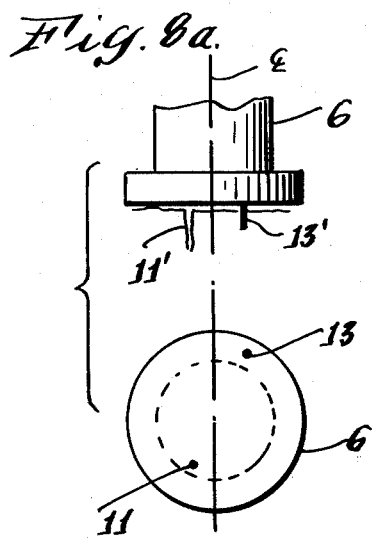
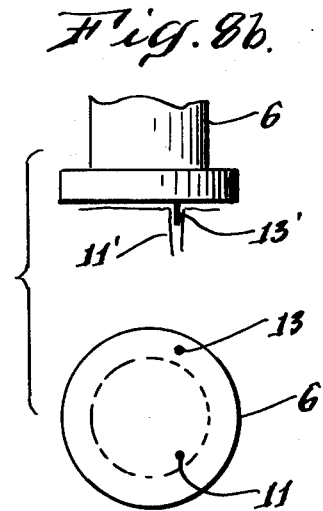
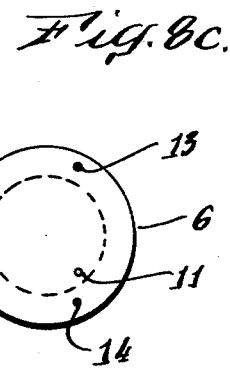
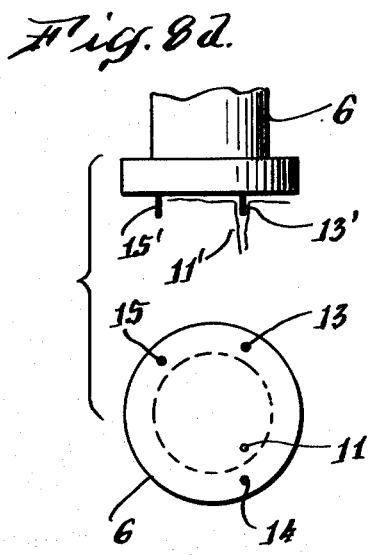
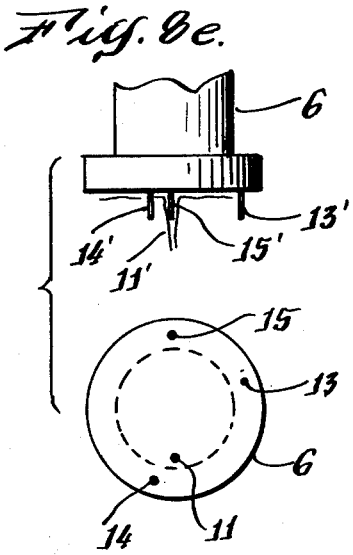
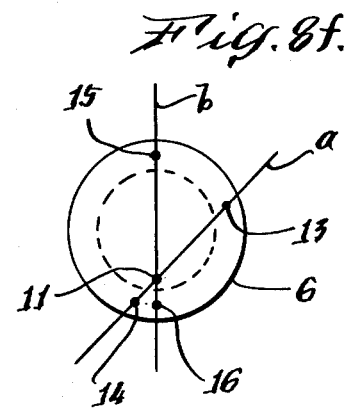

METHOD AND APPARATUS FOR DETECTING LEAKS IN HOLLOW FIBER MEMBRANE MODULES

BACKGROUND OF THE INVENTION

1. Field of the Invention

The present invention relates to a method and apparatus for detecting leaks in fluid-treating hollow fiber membrane modules without the use of liquids. More particularly, the invention relates to an optical method and apparatus for locating leaks from hollow fiber membrane modules having a housing and one or more bundles of hollow fibers positioned within the housing.

2. Brief Description of the Prior Art

Fluid separating apparatus employing hollow fiber permeable membranes are well known. Such apparatus have heretofore been employed widely for applications such as dialysis, ultrafiltration, reverse osmosis, fractionation of gaseous mixtures and the like. The permeable membranes used in such apparatus are mostly made of cellulose or its derivatives. In addition to those conventional materials, attempts have been made to utilize a variety of other materials for the fabrication of permeable membranes. Examples of such other materials include polyacrylonitrile, polymethyl methacrylate, polyvinyl alcohol, ethylene-vinyl alcohol copolymer and the like.

A large majority of such permeable membranes are of the wet type. That is, the membranes are kept wetted with an aqueous solvent from the time they are produced until the time they are put into use. If such a membrane is allowed to dry prior to being put into use, its micro-structure is irreversibly altered in a way which seriously degrades or even destroys its permeability characteristics.

Recently, dry permeable membranes, which are distinctive from the above-mentioned membranes, have been manufactured. The permeability of these dry membranes is not altered if the membrane becomes dry before it is put into use. For that reason, the dry membranes can be much more easily handled, stored and transported.

When a permeable membrane is used in a medical apparatus such as an artifical kidney, a leak in the membrane causes a loss of blood and, therefore, should be prevented by all means. For medical purposes, even a single leak per 20,000 hollow fibers in a membrane module is unacceptable. Therefore, leak tests have been performed on fluid-treating membrane modules incorporating hollow fibers. Conventional leak tests are applicable to conventional wet membranes. In such membranes, one or more bundles of hollow fibers are positioned in a case or housing with one end of each bundle being sealed by a cemented layer. A leaky fiber in such a wet membrane can be detected by submerging the cemented ends of the module into a liquid such as water. A gas such as air is applied under pressure to the external surfaces of the hollow fibers in the module. Gas passing through leaks at the cemented end of the hollow fiber bundles would be detected as bubbles in the water.

Another way of detecting leaks from conventional wet membranes is based on the fact that the gas permeability of a wet hollow fiber is low. The inlet and outlet pressures of gas applied to the module are monitored. A pressure reduction between the inlet and outlet sides of the module indicate an abnormal flow of gas due to a leak.

The above-described methods can not be used to detect leaks in dry hollow fiber membrane modules. If a dry hollow fiber is wetted and then dried, its microstructure may be so altered as to degrade or destroy its permeability properties. Furthermore, generally speaking, a dry permeable membrane has a high gas permeability. Therefore, the static pressure reduction method described above will not produce a detectable pressure difference and can not be successfully applied to dry membranes.

SUMMARY OF THE INVENTION

The problem of testing dry hollow fiber membrane modules for leaks has been solved by utilizing an optical principle which is completely different from the principles employed in the above-described conventional leak tests.

The type of fluid-treating hollow fiber membrane module which can be tested by the method and apparatus of this invention is one which includes a housing having one or more hollow fiber bundles positioned in the housing with at least one end of the bundle being sealed by a cemented layer. A gas is fed under pressure to the external surface of the hollow fibers within the housing while the fibers are dry. Gas leaking through the sealed end of the module produces refraction patterns which can be optically monitored. The apparatus for performing the optical monitoring includes a light source and means for directing light from this source along an optical path including the atmospheric volume adjacent the sealed end of the membrane module. Light which has passed through this volume is directed to an optical display. The refraction patterns of leaking gas will be visible on the display.

BRIEF DESCRIPTION OF THE DRAWINGS

While the specification concludes with claims particularly pointing out and distinctly claiming that which is regarded as the present invention, further details of preferred embodiments of the invention may be more readily ascertained from the following detailed description when read in conjunction with the accompanying drawings wherein:

FIGS. 7a, 7b and 8a through 8f illustrate alternative procedures for identifying the location of a leak at the cemented end of a fluid-treating hollow fiber membrane module in accordance with the principles of the present invention.

DETAILED DESCRIPTION OF THE PREFERRED EMBODIMENTS

A method of detecting leaks in accordance with the invention will be described generally first. A gas having a different refractive index from that of air is fed under pressure over the external surfaces of the hollow fibers to be tested. Examples of such gases include carbon dioxide gas, Freon gas and methane gas among others. When such a gas escapes through a leak in the cemented end of the module including the hollow fibers, light passing through the gas flow is refracted differently than light passing through the ambient atmosphere. As will be readily apparent, the use of a gas and of the refraction of light enables one to test a hollow fiber for leaks while the fiber is maintained in a completely dry condition. Moreover, since no chemical agents are employed except for the gas, the membrane is not contaminated.

The hollow fibers to which the method of this invention is applicable may be made of materials such as regenerated cellulose, cellulose derivatives, polyvinyl alcohol, ethylenevinly alcohol copolymer, polymethyl methacrylate, and polyacrylonitrile provided the fiber is dry. Hollow fibers containing a plasticizer also may be treated as a dry membrane in the context of this invention.

The refraction phenomenon utilized by the method of this invention can be visually monitored most advantageously by utilization of the Schlieren effect. The Schlieren effect can be used to provide optical images corresponding to the refraction of leaking gas. The Schlieren effect can be visually monitored by a variety of systems; e.g., a system utilizing one concave mirror, a system using a prism, a system using a half-mirror, a system using two concave mirrors or a direct system. Any of these systems and modifications may be utilized for purposes of the invention.

Various embodiments of optical apparatus which may be employed in the practice of this inventionn will be described with reference to the drawings.

Figure 1:
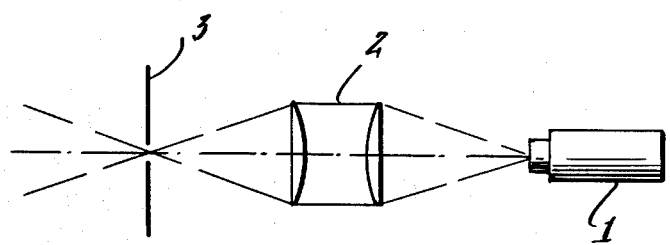
FIG. 1 is a schematic view showing one embodiment of a light source for use in the present invention.

FIG. 1 is a simplified view of a light source suitable for use in optical apparatus constructed in accordance with the present invention. The light source includes a lamp 1 which may be a conventional white light or a laser. A laser having a 20 mw output is preferred since the Schlieren images obtained when such a light source is used are so sharp that the image can be observed under normal room lighting levels making the invention more easily practiced. The light source includes beam condensing lens 2 which, while shown as a pair of plano-convex lenses, may consist of any optical components which condense light radiating from the source 1 into a beam. The beam condensing lenses may not be necessary where a laser is used. The light source may further include a shield 3 having a pin hole.

The optical path traveled by light generated by the above-described source, the manner in which the membrane module is positioned relative to the optical path and the image detecting means to be used for monitoring the refracted light are described below.

Figure 2:
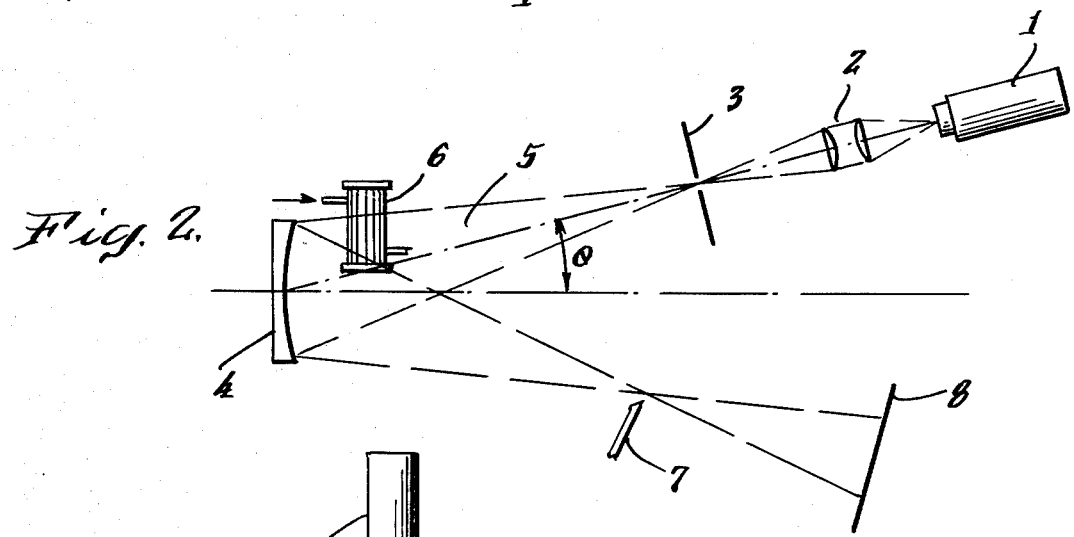
FIGS. 2–6 are schematic views of various embodiments of optical apparatus for detecting leaks in accordance with the principles of the present invention.

FIG. 2 is a schematic view of a system using a single concave mirror 4. In this arrangement, light from lamp 1 is directed along an optical axis which is preferably at a relatively small angle $\theta$ relative to a perpendicular from the midpoint of the concave mirror 4. Light directed along the optical axis passes through an atmospheric volume adjacent the cemented end of a module 6. Leaking gas which enters the atmospheric volume causes the light to be refracted differently. The light beam is reflected from the concave mirror and past a knife edge 7 onto a display screen 8. Display screen 8 provides an optical image corresponding to the gas flow (if any) from the cemented end of the module. This system is less preferred than other systems to be described below because of aberrations introduced by the lack of alignment between the optical axis of the source and the normal from concave mirror 4 and to the overlapping of images reflected from mirror 4.

Figure 3:
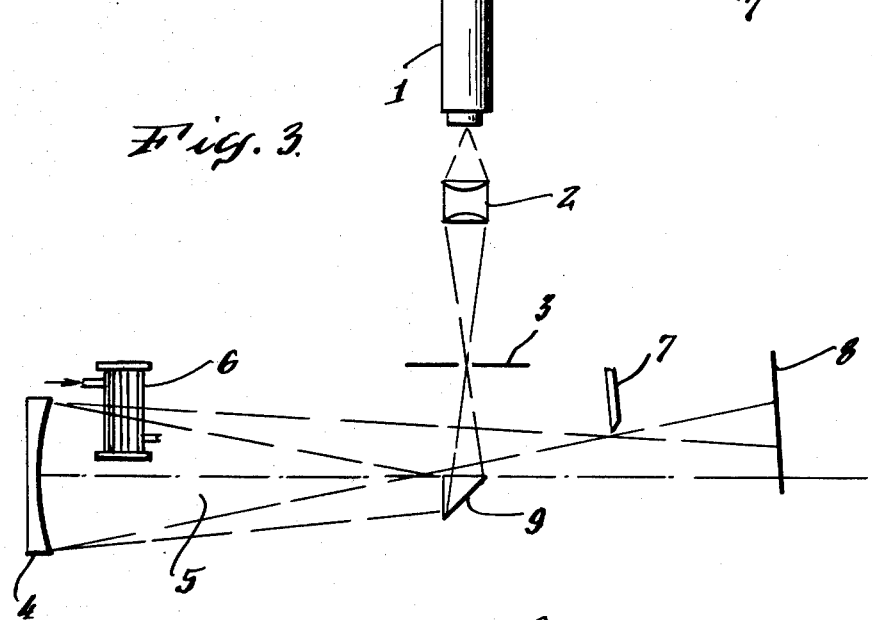

The prismatic system shown in FIG. 3 substantially eliminates the overlapping of images. In the prismatic system, light from lamp 1 is reflected through an angle of 90° by prism 9 and onto an optical path which includes the atmospheric volume adjacent the cemented end of the membrane module 6 to be tested. The light is reflected by concave mirror 4 past knife edge 7 and onto display screen 8.

Figure 4:
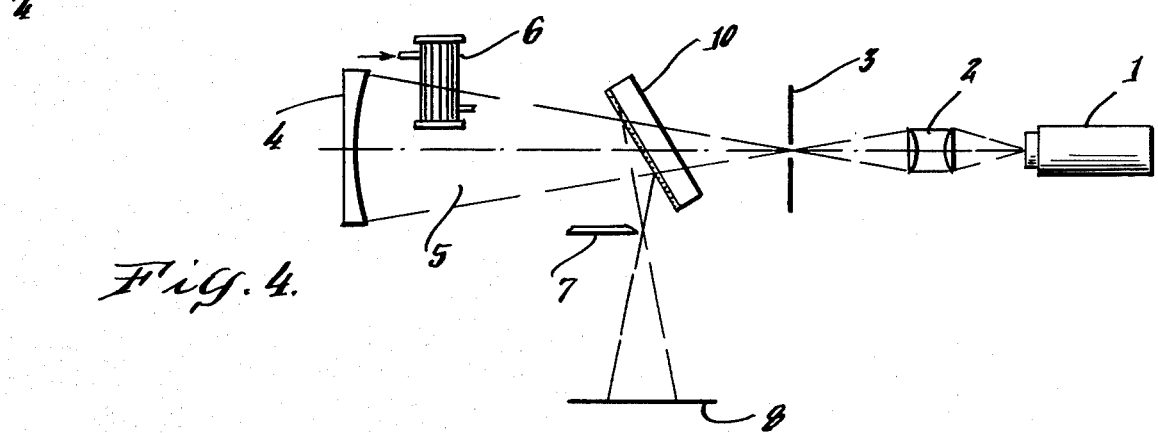

FIG. 4 shows an optical system employing a half-mirror, defined as a mirror which transmits light impinging on one surface while reflecting light impinging on the opposite surface. Light emitted from lamp 1 is transmitted through the half-mirror 10 and an atmosphere adjacent the end of the module 6 being tested to a concave mirror 4. Concave mirror 4 reflects the light back to the reflective surface of half-mirror 10 where it is reflected approximately 90° from its original optical path and past a knife edge 7 onto display screen 8. The advantages of this system are that the source optical path coincides with the refractive optical path and that the system is comparatively easy to adjust. One disadvantage of this system is that the half-mirror reduces the amount of projecting light for the image so that a dim image is obtained.

Figure 5:
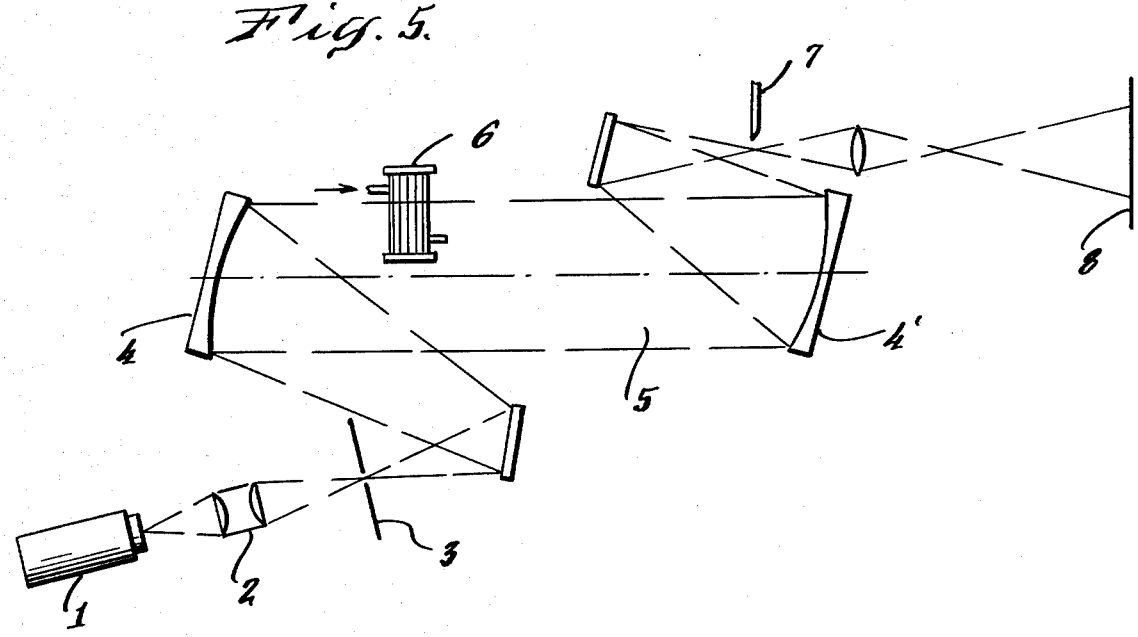

Illustrated in FIG. 5 is an optical system implying a pair of beam-collimating concave mirrors. In this system, the light from lamp 1 is collimated between the two concave mirrors 4, 4' to establish an optical path 5 of parallel rays. The image of a membrane module 6 being tested appears on an image detecting means or display screen 8. The field of this system is large and a bright image is obtained. Another advantage of this optical system is that because the optical path is composed of parallel rays, a change in the relative position of the module being tested does not affect the intensity of the image.

Figure 6:
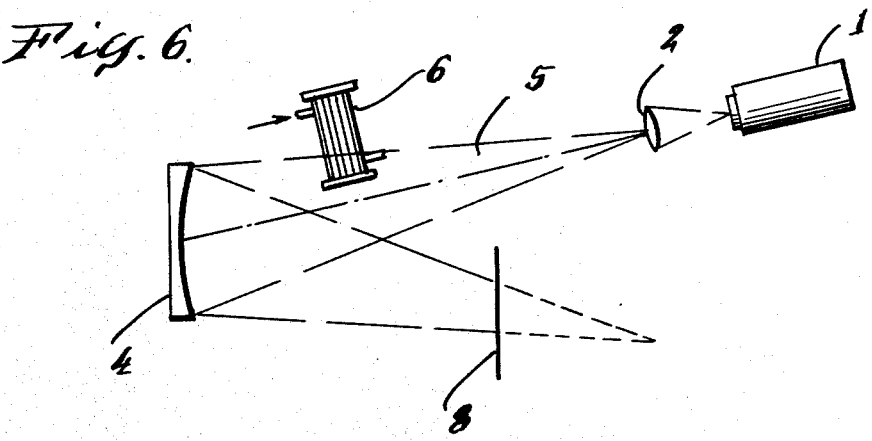

FIG. 6 shows an optical system for practicing a direct method which does not involve the use of a knife edge. A screen 8 is positioned directly in the optical path. The direct method is advantageous in that the optical system includes fewer components. The system is relatively more easily adjusted.

In any of the optical systems illustrated in FIGS. 2-6, the image detecting means may comprise a white or light-colored plain screen which is preferably made of fabric, paper or film material. A detectable image can still be obtained in these systems if the knife edge is omitted.

To support the membrane module to be tested in position within the optical path, conventional stands (not shown) may be utilized. Preferably, these stands will permit the module to be rotated within the optical path to permit the exact location of leaking openings on the cemented end to be detected.

The means for feeding pressurized gas to the external surfaces of the hollow fibers in the module may be conventional, comprising a gas cylinder, a pressure control valve, a flow meter and piping, none of which is shown, for connecting the membrane module being tested with the gas cylinder.

By means of the optical systems described above, gas leaking from the cemented end of a module being tested can be visually detected. More specifically, leaks due to a damaged hollow fiber or due to imperfect bonding between the bonding agent of the cemented layer and the hollow fiber or between the inner wall of the housing and the bonding agent can be easily detected. Generally speaking, the Schlieren method does not indicate the position of a leaky opening along an optical path. However, this disadvantage can be easily overcome.

The leaky opening is first located from the optical image obtained by projecting light when the module to be tested is oriented in a first predetermined position. Then, the module is rotated 90° about its central axis and a second optical image is obtained. The leaky opening is located at the intersection of the two lines.

The operation described above generally is described in more detail with reference to FIG. 7 which shows the side and end views of a module being tested in two different positions. A leaky opening 11 at one end of the module 6 is located at $X_i$ on an X-axis by projecting light in the X direction or into the paper in FIG. 7a. Then, the module is rotated 90° about its central axis and a second optical image is obtained. In the second optical image, the leaky opening appears on a line with $Y_i$. The exact location 12 of a leaky opening on the module end is the intersection of the lines $X_i$ and $Y_i$. The leak can be repaired in a conventional manner.

FIG. 8 shows an alternate embodiment for detecting the exact location of leaky openings. A needle or pin 13 is inserted into the cemented end of the housing away from the hollow fiber bundle (FIG. 8a) and the module is rotated about its central axis until the image 11' of a gas flow coincides with the image 13' of the inserted pin (FIG. 8b). When the images 11' and 13' coincide, a second pin 14 is set up along the same line.

A third pin 15 is inserted into another position (FIG. 8d) on the cemented end of the module. The module is again rotated about its central axis until the optical image 15' of pin 15 coincides with the image 11' produced as a result of leaking gas (FIG. 8e). A fourth pin 16 is set up in another position in line with the coinciding images 11' and 15'. A straight line a is drawn between pins 13 and 14. A second straight line b is drawn between pins 15 and 16. The intersection of the straight lines a and b pinpoints the leaky opening (FIG. 8f). The advantage of this method is that it is more readily carried out then the previously described method since the test module need not be rotated by exactly 90°. It should be understood that ink or other markings may be substituted for the second and fourth pins.

The following examples are intended to further illustrate the invention but should not be construed as limiting the invention. It should be understood that, in the fabrication of the test modules used in the examples, that leaky hollow fibers were intentionally employed.

EXAMPLE 1

5,000 dry hollow fibers of ethylene-vinyl alcohol copolymer (400 microns inner diameter, 500 microns outer diameter) were positioned in a cylindrical housing having an outer diameter of 50 millimeters. Both ends of the fiber bundles were cemented to the housing with medical grade polyurethane resin. The module was kept dry while carbon dioxide gas was fed over the external surfaces of the hollow fibers at a pressure of 0.2 kilograms per centimeter squared. The outflow of gas leaking from the openings at the cemented end of the module was monitored by the optical apparatus described with reference to FIG. 5. Modules with no leaky openings showed no abnormal outflow of gas at the cemented end. Where the modules included leaky fibers, gas flows at the cemented end were clearly observed. The exact location of the leaks were identified by rotating the housing by 90° as described above with reference to FIG. 7. The leaks were stopped by applying a polyurethane resin to the leaking openings. The modules repaired in this manner were again examined for leaks by submerging the cemented ends of the module under water and by feeding air under pressure over the external surfaces of the hollow fibers. This check revealed no leaks.

EXAMPLE 2

13,500 dry regenerated cellulose hollow fibers (200 microns inner diameter, 250 microns outer diameter) were positioned in a cylindrical housing. Both ends of the hollow fiber bundle were cemented to the housing with medical grade polyurethane resin. While this module was maintained in a dry condition, methane gas was fed to the external surfaces of the hollow fibers in the housing at a pressure of 0.3 kilograms per centimeter squared. The atmospheric volume at the cemented end of the module was monitored for leaking gas by the direct projection method described with reference to FIG. 6. Modules containing no leaky openings showed no outflow of gas. Modules containing leaky openings clearly showed the outflows of leaking gas.

The method employing reference pins as described with reference to FIG. 8 was applied to the leaking modules to find the exact location of the leaks. The leaky openings were plugged with polyurethane resin. Each of the repaired modules was thereafter fitted with a header element and the bottom inlet of the housing was closed with suitable means. The interior of the housing was filled with water. A 0.3% aqueous solution of blue-dextran was admitted into the inner side of the hollow fibers. At a pressure of 300 millimeters mercury, the module was allowed to stand for five minutes before the water was withdrawn. The concentration of blue-dextran in the drain water as established with a spectrophotometer. The concentrations were invariably found to be less than 0.001%, thus indicating that the modules had been completely repaired.

While there have been described what are considered to be preferred embodiments of the invention, variations and modification therein will occur to those skilled in the art once they become acquainted with the basic concepts of the invention. Therefore, it is intended that the appended claims shall be construed to include all such variations and modifications as fall within the true spirit and scope of the invention.

What is claimed is:

1. A method for detecting leaks from a hollow fiber membrane module comprising a housing having at least one bundle of hollow fibers positioned therein with at least one end of each said bundle being sealed by a cemented layer, said method comprising the steps of:
   directing gas under pressure over the external surfaces of the fibers within the housing, said gas having a refractive index different from the refractive index of the ambient atmosphere; and
   optically monitoring an atmospheric volume adjacent the cemented end of the module to detect any refraction patterns caused by leaks of said gas through the cemented end.

2. A method as defined in claim 1 wherein the optical monitoring is performed by a Schlieren optical system.

3. A method as defined in claim 1 wherein said step of optically monitoring the atmospheric volume includes the steps of:
   directing a light beam through the atmospheric volume;
   reflecting the light beam from a concave mirror after it has passed through the atmospheric volume; and directing the reflected beam onto a display screen where refraction patterns produced by leaking gas may be visually detected.

4. An apparatus for detecting leaks from a hollow fiber membrane module comprising a housing having at least one bundle of hollow fibers positioned therein with at least one end of each said bundle being sealed by a cemented layer, said apparatus being used when gas having a non-ambient refractive index is applied under pressure to the external surface of the fibers and comprising:

a light source;

means for directing light from said source along an optical path including the atmospheric volume adjacent the cemented end of the module;

means for displaying an optical image of the light beam which has passed through said volume, said optical image having visible refraction patterns when leaking gas enters the monitored volume due to differences between the refractive index of the gas and the refractive index of the ambient atmosphere.

5. An apparatus as defined in claim 4 wherein said light directing apparatus includes at least one concave mirror.

6. An apparatus as defined in claim 5 wherein said apparatus further includes a knife edge interposed in the light beam.

7. A method of detecting leaks from a surface of a closed body comprising the steps of:

directing a gas under pressure into the closed body, said gas having a refractive index different from the refractive index of the ambient atmosphere; and optically monitoring an atmospheric volume adjacent the surface being tested to detect any refraction patterns caused by leaks of the applied gas.

8. An apparatus for detecting leaks from the surface of a closed body, comprising:

a light source for producing a light beam;

means for directing said light beam along an optical path passing through the atmospheric volume adjacent said surface of said body;

means operably coupled with said body for supplying a gas having a non-ambient refractive index under pressure to said body; and means for displaying an optical image of the light beam which has passed through said atmospheric volume, said optical image having visible refractive patterns when gas leaking from said surface enters the monitored volume due to differences between the refractive index of the gas and the refractive index of the ambient atmosphere.

* * * * *